(12) United States Patent
Xie et al.

(10) Patent No.: US 7,875,756 B2
(45) Date of Patent: *Jan. 25, 2011

(54) PROCESS FOR PRODUCING LOWER OLEFINS UNDER NEGATIVE PRESSURE

(75) Inventors: Zaiku Xie, Shanghai (CN); Juntao Liu, Shanghai (CN); Siqing Zhong, Shanghai (CN); Wenwei Wu, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 340 days.

This patent is subject to a terminal disclaimer.

(21) Appl. No.: 11/990,401

(22) PCT Filed: Aug. 9, 2006

(86) PCT No.: PCT/CN2006/002013

§ 371 (c)(1),
(2), (4) Date: May 6, 2008

(87) PCT Pub. No.: WO2007/019787

PCT Pub. Date: Feb. 22, 2007

(65) Prior Publication Data

US 2009/0105512 A1 Apr. 23, 2009

(30) Foreign Application Priority Data

Aug. 15, 2005 (CN) .................... 2005 1 0028810

(51) Int. Cl.
*C07C 4/06* (2006.01)
(52) U.S. Cl. .................. 585/651; 585/653; 208/113; 208/120.01

(58) Field of Classification Search .......... 585/651, 585/653; 208/113, 120.01
See application file for complete search history.

(56) References Cited

U.S. PATENT DOCUMENTS

| | | | |
|---|---|---|---|
| 5,981,819 A | 11/1999 | Moeller et al. | |
| 6,222,087 B1 * | 4/2001 | Johnson et al. | 585/651 |
| 7,692,057 B2 * | 4/2010 | Xie et al. | 585/653 |
| 2003/0181777 A1 * | 9/2003 | Powers et al. | 585/648 |

FOREIGN PATENT DOCUMENTS

| | | |
|---|---|---|
| DE | 102 33 069 C1 | 9/2003 |
| JP | 61-289049 A | 12/1986 |
| WO | WO-2004/072002 A1 | 8/2004 |

* cited by examiner

*Primary Examiner*—Tam M Nguyen
(74) *Attorney, Agent, or Firm*—Birch, Stewart, Kolasch & Birch, LLP

(57) ABSTRACT

A process for producing lower olefins is disclosed. The technical problem is to overcome the defects presented in the prior art including high reaction pressure, high reaction temperature, low yield and selectivity of lower olefins as the target products, poor stability and short life of catalyst, and limited suitable feedstocks. The disclosed process, which is carried out under the conditions of catalytic cracking olefins and adopts as a feedstock an olefins-enriched mixture containing one or more C4 or higher olefins and optionally an organic oxygenate compound, comprises the steps of: a) letting the feedstock contact with a crystalline aluminosilicate catalyst having a $SiO_2/Al_2O_3$ molar ratio of at least 10, to thereby produce a reaction effluent containing lower olefins; and b) separating lower olefins from the reaction effluent; wherein, the reaction pressure is from −0.1 MPa to <0 MPa.

13 Claims, No Drawings

PROCESS FOR PRODUCING LOWER OLEFINS UNDER NEGATIVE PRESSURE

CROSS REFERENCE

The present application claims the priority of the patent application with Serial No. 200510028810.9 as filed with the State Intellectual Property Office of China on Aug. 15, 2005, which is incorporated herein for reference in its entirety for all purposes.

TECHNICAL FIELD

The present invention relates to a process for producing lower olefins, and in particular to a process for producing lower olefins by virtue of catalytic cracking of $C_4$ or higher olefins.

BACKGROUND ART

Petrochemical industry is an important supporting industry in national economy, and supplies a large quantity of chemical raw materials for various departments including industry, agriculture, communication and national defense, which is thus one of the industrial sectors taking correlative and leading action in national economy. Lower olefins are one of the most important basic raw materials constituting modern petrochemical industry.

For instance, propylene is mainly used for the production of polypropylene, cumene, oxo alcohol, acrylonitrile, propylene oxide, acrylic acid, isopropanol and etc., wherein polypropylene accounts for more than half of the demand for propylene in the world. At present, 67% of propylene in the world is derived from by-products in the production of ethylene by steam cracking, 30% of which is derived from by-products in the production of gasoline and diesel oil by catalytic cracking unit (FCC) in refinery, and low amount of which (about 3%) is obtained from dehydrogenation of propane and metathesis reaction of ethylene-butylene. It is predicted that the demand of propylene in the future will be increased in a higher rate than the supply thereof. Considering the relatively higher rate of increase in term of demand of propylene, and the situation of "demand exceeds supply" presented in conventional production modes, it is necessary to recur to other various new techniques of increasing yield of propylene for the purpose of supplementing the demand of propylene.

At present, there are quite a lot of raw materials of C4 or higher olefins in the world. Considering the influence of various factors including change of chemical product market and transportation cost, it is a preferable way to make use of these raw materials by subjecting them to deep processing on the spot. One hopeful process of which involves the conversion of C4 or higher olefins to lower olefins. The process not only can make use of raw materials of C4 or higher olefins being relatively surplus and having a lower accessory value, but also can obtain various lower olefins products having wide uses.

The reference document CN1490287A disclosed a process for production of ethylene and propylene by reacting a mixture containing $C_4$ or $C_5$ olefins in a fixed-bed reactor at a temperature of 350-500° C., a pressure of 0.6-1.0 MPa and a weight hourly space velocity (WHSV) of 1-10 hr$^{-1}$. It was focused on the modification of various types of catalysts and the reaction results, and the reaction raw materials are mainly directed to $C_4$ and $C_5$ olefins but not to $C_5$ or higher olefins. Meanwhile, a single reactor configuration was used therein, thus it was impossible to assure that the catalyst kept a desirable stability and to obtain a desirable yield of the target products.

The reference document CN1274342A (counterpart to U.S. Pat. No. 6,307,117B1) disclosed a process for producing ethylene and propylene by catalytic conversion from a linear hydrocarbon feedstock containing 20% or more of at least one $C_4$-$C_{12}$ olefins, wherein zeolite in a zeolite-containing catalyst used therein satisfied the following requirements: said zeolite contained substantially no proton, said zeolite had a $SiO_2/Al_2O_3$ molar ratio of from 200 to 5,000, and said zeolite contained at least one metal selected from the group consisting of metals belonging to Group IB of the Periodic Table, and said zeolite was an intermediate pore size zeolite, and the preferred zeolite belonged to the ZSM-5 zeolite family. The reaction was carried at a temperature of 400-700° C., a pressure of 1-10 atm and a WHSV of 1-1,000 hr$^{-1}$. However, a single reactor configuration was similarly used therein, thereby resulting in relatively lower yields of ethylene and propylene with the highest yield of propylene being only 25.19%.

The reference document WO 00/26163 to Equistar Chemicals, L.P. disclosed a process for making propylene and ethylene from a feedstock containing at least 60 wt. % $C_4$ and/or $C_5$ olefins with a zeolite catalyst having an intermediate pore size. Zeolites useful in the invention included: zeolites having one-dimensional channel such as ZSM-23 and AlPO$_4$-11 which had a pore diameter greater than 3.5 Å and a pore size index within the range of 14 to 28; and zeolites having interconnecting channels such as ZSM-57 and AlPO$_4$-18 which included a primary channel that had a pore diameter greater than 3.5 Å and a pore size index within the range of 14 to 28, and a secondary channel that had a pore size index less than 20. The catalyst could be Na-type, H-type and etc., in which trace amounts of an oxidizing metal such as Pd or Pt could be added to promote coke removal during catalyst regeneration. The process was used generally with a fixed-bed reactor system, and the reaction was preformed at a temperature of 200-750° C., a pressure of 0.05-1 MPa and a WHSV of 0.5-1,000 hr$^{-1}$. On the one side, the reference did not disclose concrete preparation method of the catalyst and reaction data. Meanwhile, a single reactor configuration was also used therein, which determined the results including non-ideal yields of ethylene and propylene and poor stability of the catalyst.

CONTENTS OF THE INVENTION

The technical problem to be solved in the present invention is to overcome the defects presented in the prior documents including high reaction pressure, high reaction temperature, low yield and selectivity of lower olefins as the target products, poor stability and short life of catalyst, and limited suitable feedstocks, and the present invention put forward a novel process for producing lower olefins. The present process is featured with lower reaction pressure and temperature, high yield and good selectivity in term of lower olefins as the target product, as well as high stability and long life of the catalyst, and could be applied to various resources of feedstock.

To solve the above problem, the technical solution of the present process is as follows: a process of producing lower olefins, which is carried out under the conditions of catalytic cracking olefins and adopts as a feedstock an olefins-enriched mixture containing one or more C4 or higher olefins, comprises the steps of:

a) letting the feedstock contact with a crystalline aluminosilicate catalyst having a $SiO_2/Al_2O_3$ molar ratio of at least 10, to thereby produce a reaction effluent containing lower olefins; and b) separating lower olefins from the reaction effluent;

wherein, the reaction pressure (gauge pressure, the same below) is from −0.1 MPa to <0 MPa.

The term "lower olefins" used herein refers to olefins having 2 to 6 carbon atoms.

The olefins-enriched mixture containing one or more C4 or higher olefins used as a feedstock in the above technical solution is preferably an olefins-enriched mixture fraction containing C4 or higher olefins and derived from catalytic cracking units in refinery or from steam cracking units in ethylene factory, or an olefins-enriched mixture component containing C4 or higher olefins and co-produced in the production of alpha-olefins, or by-produced in OTO (from oxygenate to olefin), for example MTO (methanol to olefin), such as MTP (methanol to propylene). The amount of C4 or higher olefins in the olefins-enriched feedstock ranges from 10 to 90% by weight. The olefins-enriched mixture is preferably a mixture containing $C_4$-$C_{12}$ linear olefins, more preferably a mixture containing $C_4$-$C_8$ linear olefins.

The reaction effluent herein passes in turn such as ethylene separation tower and propylene separation tower to thereby obtain lower olefins product such as ethylene and propylene. Such process of separating lower olefins is well known to a person skilled in the art.

In one preferred embodiment of the invention, an organic oxygenate compound is added into the olefins-enriched mixture, and the weight ratio of the organic oxygenate compound to olefins present in the olefins-enriched mixture is 0.01-10:1. The organic oxygenate compound used herein includes methanol, dimethyl ether, ethanol, ethyl ether or mixtures thereof in any ratio. Preferably, the organic oxygenate compound is methanol, dimethyl ether or a mixture of methanol and dimethyl ether in any ratio. One preferred embodiment of the invention resides in adding a suitable amount of an organic oxygenate compound together with the hydrocarbon feedstock to the reactor. For instance, on the one side, methanol or dimethyl ether as an oxygenate compound is dehydrated under the reaction conditions to form ethylene and propylene which is in favor of increasing the yield of the target products, and meanwhile water as produced may serve as a diluting gas for cracking C4 or higher olefins, and more importantly, methanol or dimethyl ether produces by catalytic cracking at a relatively lower temperature an active intermediate that can activate carbon-carbon bond of hydrocarbons to thereby lower the reaction temperature, and reduce carbon deposition at acidic center of the catalyst. Simultaneously, a certain amount of methanol or dimethyl ether or mixture thereof is supplemented to the effluent from the outlet of each reactor for the purpose of providing heat absorption needed in cracking reaction by the virtue of dehydration-heat liberation of the organic oxygenate compound, and at the same time providing diluting gas, so that the intermediate procedures and energy during the reactions are effectively utilized by an effective combination of two kinds of the reactions mentioned above.

In the present invention, the reaction pressure is preferably −0.08-<−0.01 MPa; the reaction temperature is preferably 400-580° C., more preferably 440-530° C.; a weight hourly space velocity (WHSV, the weight of feedstock passed per hour per unit weight of catalyst) of preferably 0.1-100 $hr^{-1}$, more preferably 1-50 $hr^{-1}$. The crystalline aluminosilicates used herein are preferably selected from ZSM type molecular sieves, beta molecular sieves or mordenite molecular sieves. The ZSM molecular sieves are more preferably selected from ZSM-5, ZSM-11, ZSM-23 or ZSM-42, most preferably ZSM-5 molecular sieves. The molecular sieves used herein have a $SiO_2/Al_2O_3$ molar ratio of preferably 10-3,000, more preferably 50-1000, most preferably 50-500.

In the present process with the operation under negative pressure, the reactor is preferably selected from axial fixed-bed reactors, radial fixed-bed reactors or moving bed reactors, more preferably from axial fixed-bed reactors or radial fixed-bed reactors.

With the operation under negative pressure, the present process could thermodynamically effectively inhibit a tendency towards polyreaction, polymerization or even condensation of olefins so as to decrease the number of olefin molecules, and instead favorably promote a tendency towards reducing sizes of olefins in the feedstock so as to produce more lower olefins as the target products. Meanwhile, during the catalytic cracking of olefins, olefins of both reactants and the target products are subject to hydrogen transfer reaction so as to produce the corresponding alkanes, which is one main reason accounting for the reduced selectivity and yield of the target products. The hydrogen transfer reaction is a kind of bimolecular reactions, and the reduction of the reaction pressure also greatly inhibits the hydrogen transfer reaction of olefins. Of a special note is that, the inhibition of the hydrogen transfer reaction plays a great role in reducing the production of coke precursors and prolonging the stability and regeneration period of the catalyst. Furthermore, the operation condition of negative pressure could also significantly reduce reaction temperature and thus effectuate a lower operational temperature condition, and obtain a higher selectivity and yield of lower olefins. The temperature involved is also a key factor to affect the activity period of a catalyst; and the lower the temperature is, the better the stability of catalyst activity and the longer the operation life of the catalyst is.

In short, the operation under negative pressure thermodynamically facilitates the reactions to decrease the molecular sizes, meanwhile, reducing the reaction temperature, which effectively inhibits the hydrogen transfer reaction of olefins. This ultimately slows down the deactivation of the catalyst due to the deposit of coke greatly, and thus prolongs the stable period of catalyst activity and obtains a higher selectivity and yield of the target products. It is very important for the process of increasing yield of lower olefins by virtue of fixed-bed catalytic cracking.

The technical solution of the invention achieves a preferable technical effect, which effectively prolongs the stable period of the catalyst activity and obtains a higher yield of lower olefins, with the reaction pressure of −0.1-<0 MPa, reaction temperature of 400° C.-580° C., and WHSV of 0.1-100 $hr^{-1}$.

Reference could be made to conventional catalytic cracking process of lower olefins with respect to other operation conditions that are not specifically described herein but may be involved in the present process for producing lower olefins by catalytic cracking.

Unless identified otherwise, the percentages and ratios used herein are all on the basis of weight.

Unless identified otherwise, the $SiO_2/Al_2O_3$ molar ratio of the crystalline aluminosilicates in the present invention is calculated on atomic basis.

All the publications mentioned are incorporated herein for reference in their entirety for all purposes.

The following examples further describe and demonstrate the preferred embodiments of the present inventions. All of the examples are merely illustrative, not interpreted as limiting to the present inventions.

In the examples, the amounts of various components in each of the mixtures involved are separated and detected with HP-6890 gas chromatograph (Agilent Technologies, Inc., the United States), equipped with a hydrogen flame ion detector and a Φ0.53 mm PLOT $Al_2O_3$ capillary chromatographic column with a length of 50 meters.

EXAMPLES

Examples 1-4

Experiments on Catalytic Cracking Reactions Under Negative Pressures, Various WHSV Conditions and with 1-Butene Feedstock Raw materials in a molar ratio of 200 $SiO_2$:0.5 $Al_2O_3$:60 n-butyl amine:17 $OH^-$:200 NaCl:6300 $H_2O$ were mixed with stirring at room temperature for 15 hr to formulate a slurry containing silicon, aluminum, template (n-butyl amine) and water in light of a $SiO_2/Al_2O_3$ molar ratio of 200. Thereafter, the slurry was crystallized at 140° C. for 50 h, followed by washing the crystallized solution with distilled water, drying it at 120° C. in an air atmosphere for 12 hr and then calcining at 580° C. in an air atmosphere for 8 hr to obtain ZSM-5 molecular sieve. 50 g of the ZSM-5 molecular weight was mixed with 87 g of 40% (weight) silica gel, and extruded to obtain strips followed by drying them at 130° C. in an air atmosphere for 12 hr and calcining at 430° C. in an air atmosphere for 6 hr to obtain a ZSM-5 type catalyst.

5 g of the above ZSM-5 type catalyst was loaded into thermostatic zone of a reactor (which is Φ18 mm axial fixed-bed reactors, the same in the following examples, unless identified otherwise), and activated at 480° C. in a $N_2$ atmosphere for 3 hr prior to reaction. Then, a pure 1-butene feedstock (99.9% purity) was charged to react by contacting with the catalyst. The reaction temperature was 500° C. and the reaction pressure was −0.042 MPa. The negative pressure was effectuated by switching on the power of a vacuum pump and adjusting its frequency converter until the desired negative pressure was achieved. The product was analyzed by sampling after reacting for 2 hr (the same in the following examples) under different reaction conditions. The reaction results were listed in Table 1.

TABLE 1

The reaction results under negative pressures and various WHSV conditions

| | Example No. | | | |
|---|---|---|---|---|
| | Example 1 | Example 2 | Example 3 | Example 4 |
| WHSV (hr$^{-1}$) | 2.000 | 7.966 | 12.101 | 19.829 |
| Conversion of C4 olefin % | 68.779 | 71.049 | 67.345 | 65.108 |
| Selectivity of ethylene % | 9.767 | 11.044 | 10.433 | 8.975 |
| Selectivity of propylene % | 31.397 | 38.109 | 43.663 | 44.353 |
| Selectivity of (E + P) % | 41.164 | 49.153 | 54.096 | 53.328 |
| Yield of ethylene % | 6.718 | 7.847 | 7.026 | 5.844 |

TABLE 1-continued

The reaction results under negative pressures and various WHSV conditions

| | Example No. | | | |
|---|---|---|---|---|
| | Example 1 | Example 2 | Example 3 | Example 4 |
| Yield of propylene % | 21.594 | 27.076 | 29.405 | 28.877 |
| Yield of (E + P) % | 28.312 | 34.923 | 36.431 | 34.720 |

Notes:
E referred to ethylene;
P referred to propylene; and
E + P referred to the sum of ethylene and propylene

Examples 5-7

Experiments on Catalytic Cracking Reactions Under Negative Pressures, Various Temperature Conditions and with the Feedstock Being Mixed $C_8$ Mono-Olefin (which was from Lanzhou Refinery of PetroChina Company Limited (Lanzhou city, China), wherein the Weight Percent of Octene was about 80.5%, and the Weight Percent of Octane was about 19.5%)

5 g of ZSM-5 type catalyst as prepared in the above Example 1 (but with a $SiO_2/Al_2O_3$ molar ratio of 800) was loaded into thermostatic zone of a Φ18 mm axial fixed-bed reactor, and activated at 480° C. in a $N_2$ atmosphere for 3 hr prior to reaction. Then, a C8 mono-olefin feedstock was charged to react by contacting with the catalyst. The negative pressure was effectuated by switching on the power of a vacuum pump and adjusting its frequency converter until the desired negative pressure was achieved. The yields and selectivity of products under the different conditions were listed in Table 2.

TABLE 2

The yields and selectivity of ethylene and propylene under different conditions with the C8 mono-olefin feedstock

| | Example No. | | |
|---|---|---|---|
| | Example 5 | Example 6 | Example 7 |
| Reaction temperature, ° C. | 480 | 460 | 450 |
| Reaction pressure, MPa | −0.06 | −0.06 | −0.06 |
| WHSV (hr$^{-1}$) | 7.627 | 9.660 | 12.372 |
| Selectivity of ethylene % | 8.189 | 5.720 | 4.679 |
| Selectivity of propylene % | 45.940 | 46.442 | 45.324 |
| Selectivity of (E + P) % | 54.129 | 52.162 | 50.002 |
| Yield of ethylene % | 5.292 | 3.551 | 2.825 |
| Yield of propylene % | 29.685 | 28.835 | 27.363 |
| Yield of (E + P) % | 34.977 | 32.387 | 30.188 |

Example 8

The various steps and conditions in this example were the same as those in Example 1, except that: the molecular sieve was ZSM-5 molecular sieve catalyst having a $SiO_2/Al_2O_3$ molar ratio of 58; the reaction temperature was 410° C., the WHSV was 0.52 hr$^{-1}$ and the reaction pressure was −0.09 MPa. The negative pressure was effectuated by switching on the power of a vacuum pump and adjusting its frequency converter until the desired negative pressure was achieved. The feedstock used herein was the mixed $C_4$ feedstock obtained from FCC apparatus in Shanghai Petrochemical Refinery of SINOPEC (Shanghai city, China), whose components by weight percent were shown in Table 3. The reaction results were as follows: the yield of ethylene was 4.31%, and the yield of propylene was 25.76%.

TABLE 3

The weight percent amounts of components in the above mixed $C_4$ feedstock obtained from the above FCC apparatus

| Components | Amount, weight % | Components | amount, weight % |
|---|---|---|---|
| Isobutane | 3.249 | 1-butene | 51.857 |
| n-Butane | 13.368 | Isobutene | 0.048 |
| Propadiene | 0.068 | Cis-2-butene | 13.211 |
| Acetylene | 0.008 | Isopentane | 0.002 |
| Neopentane | 0.149 | n-Pentane | 0.000 |
| Trans-2-butene | 17.259 | 1,3-butadiene | 0.110 |
| Pentene and isohexane | 0.127 | Methylacetylene | 0.004 |
| n-Hexane | 0.007 | $C_6$ or higher | 0.531 |

Example 9

The various steps and conditions in this example were the same as those in Example 1, except that: the molecular sieve was ZSM-5 molecular sieve catalyst having a $SiO_2/Al_2O_3$ molar ratio of 950; the reaction temperature was 530° C., the WHSV was 47 $hr^{-1}$ and the reaction pressure was −0.01 MPa. The negative pressure was effectuated by switching on the power of a vacuum pump and adjusting its frequency converter until the desired negative pressure was achieved. The feedstock used herein was the mixed $C_4$ feedstock obtained from the above FCC apparatus, whose components by weight percent were shown in Table 3. The reaction results were as follows: the yield of ethylene was 5.55%, and the yield of propylene was 26.83%.

Example 10

The various steps and conditions in this example were the same as those in Example 1, except that: the molecular sieve was ZSM-5 molecular sieve catalyst having a $SiO_2/Al_2O_3$ molar ratio of 115; the reaction temperature was 500° C., the WHSV was 3 $hr^{-1}$ and the reaction pressure was −0.053 MPa. The negative pressure was effectuated by switching on the power of a vacuum pump and adjusting its frequency converter until the desired negative pressure was achieved. The feedstock used herein was the mixed $C_4$ feedstock obtained from the above FCC apparatus, whose components by weight percent were shown in Table 3. The reaction results were as follows: the yield of ethylene was 7.34%, and the yield of propylene was 30.51%.

Example 11

The various steps and conditions in this example were the same as those in Example 1, except that: the molecular sieve was ZSM-5 molecular sieve catalyst having a $SiO_2/Al_2O_3$ molar ratio of 115; the reaction temperature was 500° C., the WHSV was 3 $hr^{-1}$ and the reaction pressure was −0.053 MPa. The negative pressure was effectuated by switching on the power of a vacuum pump and adjusting its frequency converter until the desired negative pressure was achieved. The feedstock used herein was the mixed $C_4$ feedstock obtained from the above FCC apparatus, whose components by weight percent were shown in Table 3. At the same time, methanol was added together with the mixed C4 feedstock with the weight ratio of olefins in the mixed C4 feedstock to methanol of 4:1. The reaction results were as follows: the yield of ethylene was 7.89%, and the yield of propylene was 33.78%.

Example 12

The various steps and conditions in this example were the same as those in Example 1, except that: the molecular sieve was ZSM-5 molecular sieve catalyst having a $SiO_2/Al_2O_3$ molar ratio of 500; the reaction temperature was 580° C., the WHSV was 20 $hr^{-1}$ and the reaction pressure was −0.08 MPa. The negative pressure was effectuated by switching on the power of a vacuum pump and adjusting its frequency converter until the desired negative pressure was achieved. The feedstock used herein was the mixed $C_4$ feedstock obtained from the above FCC apparatus whose components by weight percent were shown in Table 3. The reaction results were as follows: the yield of ethylene was 10.82%, and the yield of propylene was 36.51%.

Example 13

The various steps and conditions in this example were the same as those in Example 1, except that: the molecular sieve was ZSM-11 molecular sieve catalyst having a $SiO_2/Al_2O_3$ molar ratio of 600; the reaction temperature was 510° C., the WHSV was 18 $hr^{-1}$ and the reaction pressure was −0.02 MPa. The negative pressure was effectuated by switching on the power of a vacuum pump and adjusting its frequency converter until the desired negative pressure was achieved. The feedstock used herein was the mixed $C_5$ feedstock (wherein the weight amount of n-pentene was 44.1%, that of n-pentane was 15.28%, and that of isopentane was 40.62%) obtained from steam cracking unit in Ethylene Factory of SINOPEC SHANGHAI Petrochemical Company Limited (Shanghai city, China). The reaction results were as follows: the yield of ethylene was 4.06%, the yield of propylene was 25.76%, and the yield of butene was 30%.

Example 14

The various steps and conditions in this example were the same as those in Example 1, except that: the molecular sieve was ZSM-42 molecular sieve catalyst having a $SiO_2/Al_2O_3$ molar ratio of 210; the reaction temperature was 530° C., the WHSV was 30 $hr^{-1}$ and the reaction pressure was −0.062 MPa. The negative pressure was effectuated by switching on the power of a vacuum pump and adjusting its frequency converter until the desired negative pressure was achieved. The feedstock used herein was the pure 1-butene (99.9% purity). The reaction results were as follows: the yield of ethylene was 6.34%, and the yield of propylene was 32.58%.

Example 15

The various steps and conditions in this example were the same as those in Example 1, except that: the molecular sieve was beta molecular sieve catalyst having a $SiO_2/Al_2O_3$ molar ratio of 800; the reaction temperature was 410° C., the WHSV was 50 $hr^{-1}$ and the reaction pressure was −0.023 MPa. The negative pressure was effectuated by switching on the power of a vacuum pump and adjusting its frequency converter until the desired negative pressure was achieved. The feedstock used herein was the mixed $C_4$ feedstock obtained from the above FCC apparatus, whose components by weight percent were shown in Table 3. The reaction results were as follows: the yield of ethylene was 3.78%, and the yield of propylene was 23.18%.

Example 16

The various steps and conditions in this example were the same as those in Example 1, except that: the molecular sieve was mordenite molecular sieve catalyst having a $SiO_2/Al_2O_3$ molar ratio of 50; the reaction temperature was 580° C., the WHSV was 0.5 $hr^{-1}$ and the reaction pressure was −0.042 MPa. The negative pressure was effectuated by switching on the power of a vacuum pump and adjusting its frequency converter until the desired negative pressure was achieved. The feedstock used herein was the mixed $C_4$ feedstock obtained from the above FCC apparatus whose components by weight percent were shown in Table 3. The reaction results were as follows: the yield of ethylene was 8.45%, and the yield of propylene was 31.36%.

Example 17

Experiment on the Cracking Performance of Catalyst with Feedstock for Catalytic Cracking being $C_4$-$C_7$ Mono-Olefins The various steps and conditions in this example were the same as those in Example 1, except that: the molecular sieve was ZSM-5 molecular sieve catalyst having a $SiO_2/Al_2O_3$ molar ratio of 180; and the feedstock was $C_4$-$C_7$ mono-olefins obtained from by-products in the production of olefins by cracking methanol (MTO) in Shanghai Research Institute of Petrochemical Technology SINOPEC (Shanghai city, China), wherein the amounts of $C_4$ and $C_5$ olefins were respectively about 60% and about 25%, with the remaining about 15% being $C_6$ or higher olefins.

5 g of the above ZSM-5 type catalyst was loaded into thermostatic zone of a Φ18 mm axial fixed-bed reactor, and activated at 480° C. in a $N_2$ atmosphere for 3 hr prior to reaction. Then, the above feedstock was charged to react by contacting with the catalyst. The reaction temperature was 530° C. and the reaction pressure was −0.068 MPa. The negative pressure was effectuated by switching on the power of a vacuum pump and adjusting its frequency converter until the desired negative pressure was achieved. The reaction results were as follows: the yield of ethylene was 8.34%, and the yield of propylene was 33.95%, and the conversion of total olefins was 72%.

Example 18

The various steps and conditions in this example were the same as those in Example 1 to produce ZSM-5 molecular sieve catalyst. 5 g of the above ZSM-5 type catalyst was loaded into thermostatic zone of a Φ18 mm axial fixed-bed reactor, and activated at 480° C. in a $N_2$ atmosphere for 3 hr prior to reaction. Then, the feedstock was charged to react by contacting with the catalyst. The feedstock used herein was the mixed $C_4$ feedstock obtained from the above FCC apparatus, whose components by weight percent were shown in Table 3. The reaction temperature was 560° C., the WHSV was 8 $hr^{-1}$ and the reaction pressure was −0.028 MPa. The negative pressure was effectuated by switching on the power of a vacuum pump and adjusting its frequency converter until the desired negative pressure was achieved. The reaction activities of the catalyst at different time points were listed in Table 4.

TABLE 4

Experiments on the life of the catalyst

| Reaction time (hr) | Yield of propylene, % | Yield of ethylene, % |
| --- | --- | --- |
| 4 | 7 | 29.9 |
| 26 | 7.4 | 29.1 |
| 50 | 7.6 | 29.4 |
| 82 | 7.2 | 28.5 |
| 150 | 7.5 | 29.9 |
| 220 | 7.5 | 30 |
| 280 | 7.6 | 30.6 |
| 320 | 7.3 | 29.4 |
| 400 | 7.5 | 30.2 |
| 440 | 7.5 | 29.9 |
| 498 | 7.3 | 29.6 |

Comparative Example 1

The various steps, conditions, catalyst and feedstock in this example were the same as those in Example 18 to investigate the so-prepared ZSM-5 catalyst, except that the reaction pressure is normal pressure. The reaction activities of the catalyst at different time points were listed in Table 5.

TABLE 5

Experiments on life of the catalyst

| Reaction time (hr) | Yield of propylene, % | Yield of ethylene, % |
| --- | --- | --- |
| 1.01 | 7.23 | 28.3 |
| 5.08 | 7.43 | 28.40 |
| 8.12 | 7.71 | 28.16 |
| 17.17 | 7.62 | 27.74 |
| 25.23 | 7.64 | 27.21 |
| 33.12 | 7.44 | 28.35 |
| 41.12 | 6.96 | 27.08 |
| 49.13 | 6.37 | 26.05 |
| 57.33 | 5.35 | 24.17 |
| 65.25 | 4.83 | 22.88 |
| 73.25 | 3.58 | 19.17 |
| 81.15 | 2.55 | 15.69 |
| 89.17 | 1.60 | 11.47 |
| 97.17 | 1.08 | 8.71 |
| 105.08 | 0.61 | 5.80 |
| 108.17 | 0.53 | 5.14 |

Obviously, the present technical solution of adding methanol could similarly markedly prolong the active period of the catalyst, which had obvious technical advantage.

Comparative Examples 2-5

The various steps, conditions, catalyst and feedstock in these experiments were the same as those in Example 1 to investigate the so-prepared ZSM-5 catalyst, except that the reaction pressure is normal pressure. The reaction activities of the catalyst at different time points were listed in Table 6.

TABLE 6

The reaction results under negative pressures and various WHSV conditions

| | Example No. | | | |
| --- | --- | --- | --- | --- |
| | Comparative Example 2 | Comparative Example 3 | Comparative Example 4 | Comparative Example 5 |
| WHSV ($hr^{-1}$) | 2.000 | 7.966 | 12.101 | 19.829 |
| Conversion of | 64.941 | 75.919 | 72.625 | 70.303 |

TABLE 6-continued

The reaction results under negative pressures and various WHSV conditions

| | Example No. | | | |
|---|---|---|---|---|
| | Comparative Example 2 | Comparative Example 3 | Comparative Example 4 | Comparative Example 5 |
| C4 olefin % | | | | |
| Selectivity of ethylene % | 7.336 | 10.003 | 11.035 | 9.526 |
| Selectivity of propylene % | 25.160 | 28.484 | 35.085 | 37.130 |
| Selectivity of (E + P) % | 32.495 | 38.487 | 46.121 | 46.655 |
| Yield of ethylene % | 4.764 | 7.594 | 8.014 | 6.697 |
| Yield of propylene % | 16.339 | 21.625 | 25.481 | 26.103 |
| Yield of (E + P) % | 21.103 | 29.219 | 33.495 | 32.800 |

Comparative Example 6

The various steps and conditions in this example were the same as those in Example 13, except that the reaction pressure is normal pressure. The reaction results were as follows: the yield of ethylene was 3.73%, and the yield of propylene was 22.89%, and the yield of butene was 26.3%.

The invention claimed is:

1. A process of producing lower olefins, which is carried out under the conditions of catalytic cracking olefins and adopts as a feedstock an olefins-enriched mixture containing one or more C4 or higher olefins, comprises the steps of:
   a) letting the feedstock contact with a crystalline aluminosilicate catalyst having a $SiO_2/Al_2O_3$ molar ratio of at least 10, to thereby produce a reaction effluent containing lower olefins; and
   b) separating lower olefins from the reaction effluent;
   wherein the reaction pressure is from −0.08 MPa to <0 MPa.

2. The process as claimed in claim 1, wherein the olefins-enriched mixture is an olefins-enriched mixture fraction containing C4 or higher olefins and derived from catalytic cracking units in refinery or from steam cracking units in ethylene factory, or an olefins-enriched mixture component containing C4 or higher olefins and co-produced in the production of alpha-olefins, or by-produced in oxygenate to olefin.

3. The process as claimed in claim 1, wherein the olefins-enriched mixture is a mixture containing $C_4$-$C_{12}$ linear olefins.

4. The process as claimed in claim 3, wherein the olefins-enriched mixture is a mixture containing $C_4$-$C_8$ linear olefins.

5. The process as claimed in claim 1, the reaction pressure is from −0.08 to <−0.01 MPa.

6. The process as claimed in claim 1, wherein the reaction temperature is 400-580° C., and WHSV is 0.1-100 $hr^{-1}$.

7. The process as claimed in claim 6, wherein the reaction temperature is 440-530° C., and WHSV is 1-50 $h^{-1}$.

8. The process as claimed in claim 1, wherein the crystalline aluminosilicates are selected from ZSM molecular sieves, beta molecular sieves or mordenite molecular sieves; and the molecular sieve has a $SiO_2/Al_2O_3$ molar ratio of 10-3,000.

9. The process as claimed in claim 8, wherein the ZSM molecular sieve is selected from ZSM-5, ZSM-11, ZSM-23 or ZSM-42; and the molecular sieve has a $SiO_2/Al_2O_3$ molar ratio of 50-1,000.

10. The process as claimed in claim 9, wherein the ZSM molecular sieve is selected from ZSM-5 molecular sieves having a $SiO_2/Al_2O_3$ molar ratio of 50-500.

11. The process as claimed in claim 1, wherein an organic oxygenate compound is added into the olefins-enriched mixture, and the weight ratio of the organic oxygenate compound to olefins present in the olefins-enriched mixture is 0.01-10:1.

12. The process as claimed in claim 11, wherein the organic oxygenate compound is methanol, dimethyl ether, or mixture of methanol and dimethyl ether.

13. The process as claimed in claim 1, wherein reactors for said catalytic cracking olefins are selected from axial fixed-bed reactors, radial fixed-bed reactors, and moving bed reactors.

* * * * *